United States Patent
Winsel et al.

(10) Patent No.: US 6,476,268 B1
(45) Date of Patent: Nov. 5, 2002

(54) PREPARATION OF N-BENZYLAMINES

(75) Inventors: Harald Winsel, Birkenheide; Wolfgang Siegel, Limburgerhof; Michael Bartsch, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/106,390

(22) Filed: Mar. 27, 2002

(30) Foreign Application Priority Data

Apr. 4, 2001 (DE) .......................................... 101 16 816

(51) Int. Cl.[7] ............................................ C07C 209/00
(52) U.S. Cl. ........................ 564/385; 564/386; 564/389; 564/391
(58) Field of Search ................................. 564/385, 386, 564/389, 391

(56) References Cited

PUBLICATIONS

Organic Process Research & Development, 2000, 4, 594–595; Huckabee et al.

*Primary Examiner*—Samuel Barts
(74) *Attorney, Agent, or Firm*—Keil & Weinkauf

(57) ABSTRACT

N-Benzylamines are prepared by a process in which
(i) in a first step, a benzaldehyde is reacted with a primary amine to give the imine and
(ii) in a second step, the imine is hydrogenated with hydrogen in the presence of a catalyst containing one or more metals of groups 8 to 10 of the Periodic Table of the Elements to give the N-benzylamine, wherein the iminization (i) is carried out in a water-miscible solvent and the resulting water of reaction is not removed, and the hydrogenation (ii) is carried out in the imine solution obtained in the iminization (i) and containing water of reaction.

7 Claims, No Drawings

PREPARATION OF N-BENZYLAMINES

The invention relates to a process for the preparation of N-benzylamines.

It is known that N-benzyl-α-methylbenzylamine can be prepared by iminization of benzaldehyde with α-methylbenzylamine and subsequent hydrogenation of the imine formed. Such a process is described by Huckabee et al., Organic Process Research & Development 4 (2000), 594–595. Optically pure (R)- and (S)-N-benzyl-α-methylbenzylamine are obtained from benzaldehyde and (R)- and (S)-α-phenylethylamine, respectively, by palladium-catalyzed hydrogenation of benzylidene(1-phenylethyl)imine formed as an intermediate. The iminization is carried out in toluene as a solvent, and the resulting water of reaction is removed by azeotropic distillation.

It is an object of the present invention to provide a simpler process for the preparation of N-benzylamines.

We have found that this object is achieved by a process for the preparation of N-benzylamines, in which (i) in a first step, a benzaldehyde is reacted with a primary amine to give the imine and (ii) in a second step, the imine is hydrogenated with hydrogen in the presence of a catalyst containing one or more metals of groups 8 to 10 of the Periodic Table of the Elements to give the N-benzylamine, wherein the iminization (i) is carried out in a water-miscible solvent and the resulting water of reaction is not removed, and the hydrogenation (ii) is carried out in the imine solution obtained in the iminization (i) and containing water of reaction.

Preferred N-benzylamines prepared by the novel process are those of the formula (I)

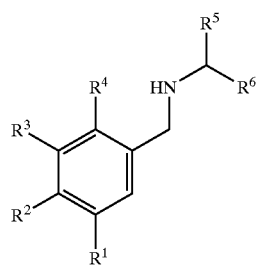

(I)

where $R^1$, $R^2$, $R^3$ and $R^4$, independently of one another, are each H, halogen or $C_1$–$C_4$-alkyl or $C_1$–$C_4$-alkoxy, each of which is unsubstituted or mono- or polysubstituted by halogen, $R^5$ is H or $C_1$–$C_8$-alkyl and $R^6$ is H, $C_1$–$C_8$-alkyl or $C_5$–$C_{12}$-aryl or $C_5$–$C_{12}$-cycloalkyl, each of which may be mono- or polysubstituted by halogen, OH or $C_1$–$C_4$-alkyl and/or $C_1$–$C_4$-alkoxy, each of which is unsubstituted or mono- or polysubstituted by halogen, or is $C_1$–$C_4$-alkoxy- or benzyloxy-substituted $C_1$–$C_4$-alkyl.

These are obtained by a procedure in which p1 (i) in a first step, a benzaldehyde of the formula (II) is reacted with an amine of the formula (III)

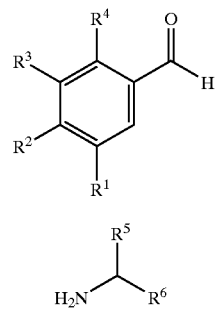

(II)

(III)

to give an imine of the formula (IV)

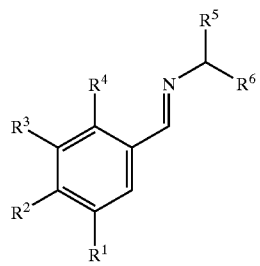

(IV)

where $R^1$–$R^6$ have the abovementioned meanings, and (ii) in a second step, the imine of the formula (IV) is hydrogenated with hydrogen in the presence of a catalyst containing one or more metals of groups 8 to 10 of the Periodic Table of the Elements to give the N-benzylamine of the formula (I), the iminization (i) being carried out in a water-miscible solvent and the resulting water of reaction not being removed, and the hydrogenation (ii) being carried out in the imine (IV) solution solution obtained in the iminization (i) and containing water of reaction.

In a first step (i), a benzaldehyde, preferably a benzaldehyde of the formula (II), is reacted with an amine, preferably an amine of the formula (III), to give an imine, preferably of the formula (IV). $R^1$ to $R^4$ are, for example, fluorine, chlorine, bromine, iodine, methyl, trifluoromethyl, ethyl, n-propyl, isopropyl, n-butyl, isobutyl, sec-butyl, tert-butyl or the corresponding alkoxy radicals. The benzaldehydes (II) may be up to tetrasubstituted but are preferably unsubstituted or mono- or disubstituted. Benzaldehydes of the formula (II) are, for example, benzaldehyde, 4-methoxybenzaldehyde, 4-tert-butylbenzaldehyde, 4-methylbenzaldehyde, 4-chlorobenzaldehyde, 4-fluorobenzaldehyde, 3-fluorobenzaldehyde, 3,5-difluorobenzaldehyde, 4-trifluoromethylbenzaldehyde and 3,5-bistrifluoromethylbenzaldehyde.

$R^5$ and $R^6$ are, for example, methyl, ethyl, propyl, isopropyl, 1- or 2-butyl, 1-, 2- or 3-pentyl, 1-, 2- or 3-hexyl, 1-, 2-, 3- or 4-heptyl or 1-, 2-, 3- or 4-octyl. $R^6$ may furthermore be $C_5$–$C_{12}$-aryl or $C_5$–$C_{12}$-cycloalkyl which is unsubstituted or mono- or polysubstituted, preferably mono- or disubstituted, by OH, said halogens or said unsubstituted or substituted $C_1$–$C_4$-alkyl or $C_1$–$C_4$-alkoxy radicals, e.g. phenyl, naphthyl, tetrahydronaphthyl, indyl, cyclopentyl or cyclohexyl which is unsubstituted or substituted in this manner. Amines of the formula (III) are, for example, α-phenylethylamine, 1-(4-methylphenyl)ethylamine, 2-heptylamine, 1-(4-chlorophenyl)ethylamine, 1-phenylpropylamine, 2-amino-3,3-dimethylbutane, 1-(1-naphthyl)ethylamine, 1,2,3,4-tetrahydronaphthylamine, 1-(4-methoxyphenyl)ethylamine, aminocyclopentanol, aminocyclohexanol, 1-aminoindane, 1-(2,4-dichlorophenyl) ethylamine, 1-benzyloxy-2-aminopropane, 1-benzyloxy-3-aminobutane, 1-(2-naphthyl)ethylamine, 1-(3,5-bistrifluoromethylphenyl)ethylamine and 1-(4-fluorophenyl)ethylamine.

The iminization (i) is carried out in the homogeneous phase in a water-miscible solvent. Suitable water-miscible solvents are methanol, ethanol, n-propanol, isopropanol, glycol, tert-butanol, THF, glycol monoalkyl ethers or glycol dialkyl ethers, such as dimethoxyethane. Preferred solvents are methanol, ethanol, n-propanol and isopropanol, and a particularly preferred solvent is methanol. Usually, the concentration of the benzaldehyde (II) and that of the amine (III) together is from 10 to 65% by weight.

The iminization (i) is preferably carried out at from 10 to 40° C., particularly preferably from 20 to 30° C., and preferably at atmospheric pressure. A reaction time of from 0.1 to 5 hours is usually sufficient for the iminization (i).

Without prior removal of the water of reaction, the imine formed is hydrogenated, after the iminization, with hydrogen in the presence of a palladium-containing catalyst in the imine solution containing the water of reaction. Suitable catalysts contain one or more metals of groups 8 to 10 of the Periodic Table of the Elements on any desired conventional inorganic support, such as alumina, silica, zirconium dioxide, titanium dioxide or carbon. Preferred catalysts contain platinum, palladium, nickel or rhodium on an inorganic support, palladium on active carbon being particularly preferred.

The hydrogenation (ii) is preferably carried out at from 10 to 40° C., particularly preferably at from 20 to 30° C., the hydrogen pressure usually being from 0.1 to 25, preferably from 0.1 to 5, bar. A reaction time of from 1 to 100 hours is usually sufficient for the hydrogenation.

The hydrogenation catalyst can be added before or after the iminization (i). The process can be operated continuously or batchwise and takes place without racemization when chiral amines are used.

As a result of the omission of the azeotropic distillation, the imine formed as an intermediate is not subjected to thermal stress. Furthermore, the novel process is easier to carry out than the process disclosed in the prior art since the process does not include the azeotropic distillation as an operation.

The examples which follow illustrate the invention.

EXAMPLES

Example 1

Batchwise Synthesis of N-4-methoxybenzyl-1-phenylethylamine

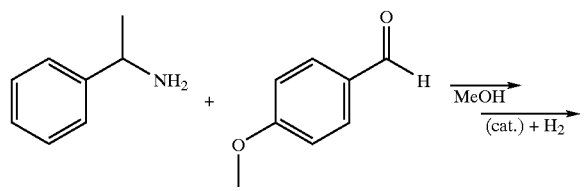

-continued

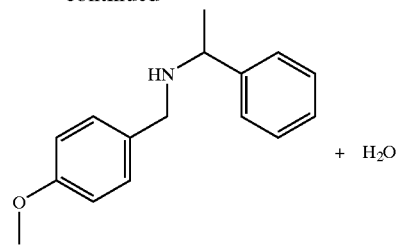
+ H₂O 100 ml of methanol and 100 mmol of 1-phenylethylamine are initially taken, and 100 mmol of 4-methoxybenzaldehyde are added dropwise at 24° C. in the course of 15 minutes. Stirring is effected for 6 hours at 24° C., the completeness of the iminization is checked by GC, 0.5 g of Pd/C (10% by weight) is added and the crude mixture is hydrogenated with hydrogen for 5 hours at atmospheric pressure. A sample is taken and the composition is investigated by GC analysis.

GC analysis results (in GC percent by area):

| | |
|---|---|
| 1-Phenylethylamine | 4.7% |
| 4-Methoxybenzaldehyde | 0.2% |
| N-4-Methoxybenzyl-1-phenylethylamine | 89.5% |

Example 2

Batchwise Synthesis of N-benzyl-1-(4-methylphenyl)ethylamine

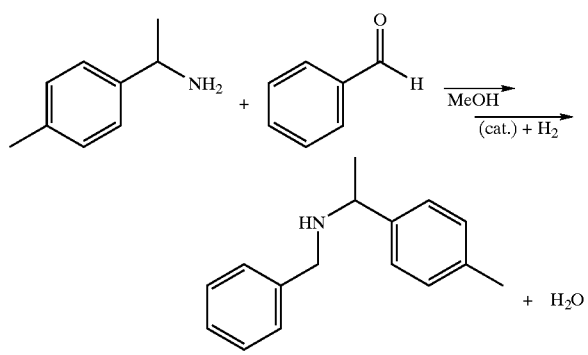
+ H₂O 100 ml of methanol and 100 mmol of 4-methyl-1-phenylethylamine are initially taken, and 100 mmol of benzaldehyde are added dropwise at 24° C. in the course of 15 minutes. Stirring is effected for 6 hours at 24° C., the completeness of the iminization is checked by GC, 0.5 g of Pd/C (10% by weight) is added and the crude mixture is hydrogenated with hydrogen for 5 hours at atmospheric pressure. A sample is taken and the composition is investigated by GC analysis.

GC analysis results (in GC percent by area):

| | |
|---|---|
| 4-Methyl-1-phenylethylamine | 5.1% |
| Benzaldehyde | 1.3% |
| N-Benzyl-1-(4-methylphenyl)ethylamine | 82.5% |

Example 3

Batchwise Synthesis of (R)-N-benzyl-1-phenylethylamine

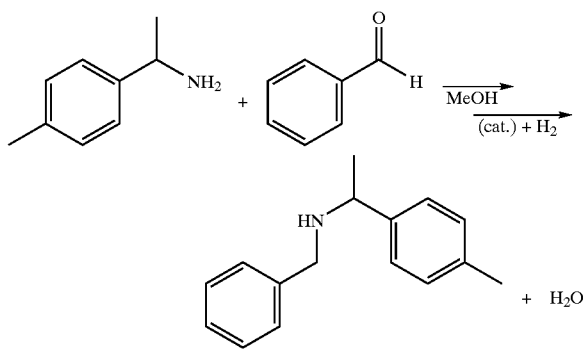

412 kg of methanol and 375.7 kg of (R)-1-phenylethylamine (ee=97.1%) are initially taken and 329 kg of benzaldehyde are added dropwise at 24° C. in the course of 120 minutes. Stirring is effected for 6 hours at 24° C., the completeness of the iminization is checked by GC, 6 kg of Pd/C (5% by weight) are added and the crude mixture is hydrogenated with hydrogen for 24 hours at atmospheric pressure. The sample is taken and the composition is investigated by GC analysis.

GC analysis results (in GC percent by area):

| | |
|---|---|
| (R)-1-Phenylethylamine | 0% |
| Benzaldehyde | 0.1% |
| (R)-N-Benzyl-1-phenylethylamine | 99.4% |
| ee = 97.1% | |

Example 4

Batchwise Synthesis of N-benzyl-2-methylhexylamine

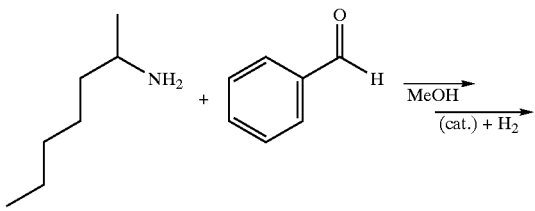

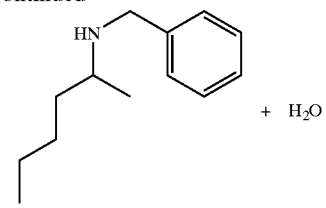

100 ml of methanol and 100 mmol of 2-heptylamine are initially taken and 100 mmol of benzaldehyde are added dropwise at 24° C. in the course of 15 minutes. Stirring is effected for 6 hours at 24° C., the completeness of the iminization is checked by GC, 0.5 g of Pd/C (10% by weight) is added and the crude mixture is hydrogenated with hydrogen for 5 hours at atmospheric pressure. A sample is taken and the composition is investigated by GC analysis.

GC analysis results (in GC percent by area):

| | |
|---|---|
| 2-Heptylamine | 0.6% |
| Benzaldehyde | 0.0% |
| N-Benzyl-2-methylhexylamine | 97.8% |

Example 5

Batchwise Synthesis of N-benzyl-1-naphthylethylamine

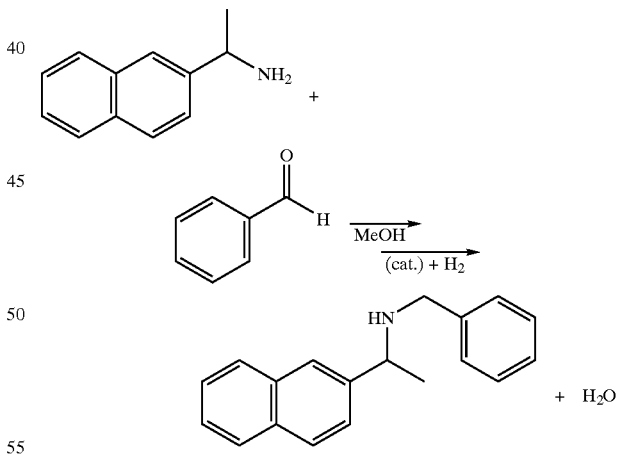

100 ml of methanol and 350 mmol of 1-naphthylethylamine are initially taken and 350 mmol of benzaldehyde are added dropwise at 24° C. in the course of 15 minutes. Stirring is effected for 6 hours at 24° C., the completeness of the iminization is checked by GC, 0.5 g of Pd/C (10% by weight) is added and the crude mixture is hydrogenated with hydrogen for 5 hours at atmospheric pressure. A sample is taken and the composition is investigated by GC analysis.

GC analysis results (in GC percent by area):

| 1-Naphthylethylamine | 0.6% |
|---|---|
| Benzaldehyde | 0.0% |
| N-Benzyl-1-naphthylethylamine | 94.3% |

Example 6

Continuous Synthesis of (S)-N-benzyl-1-phenylethylamine

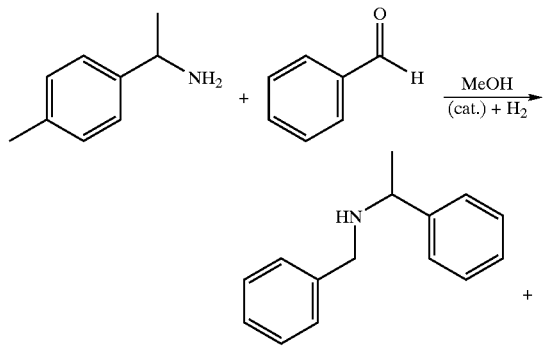

1185 g of methanol, 605.9 g of (S)-phenylethylamine (ee=99.2%) and 530.6 g of benzaldehyde are mixed at room temperature and, after 30 minutes, the resulting imine is hydrogenated in a fixed-bed tubular reactor at room temperature and 10 bar hydrogen pressure over 144 g of a palladium-containing hydrogenation catalyst (1% by weight of Pd, 10% by weight of MgO on $Al_2O_3$) to give the (S)-N-benzylphenylethylamine. A sample is taken at the reactor exit and the composition is investigated by GC analysis. Working up is carried out by distillation.

GC analysis results (in GC percent by area):

| (S)-Phenylethylamine | 0.1% |
|---|---|
| Benzaldehyde | 0% |
| (S)-N-Benzyl-1-phenylethylamine | 98.3% |
| ee = 99.1% | |

We claim:

1. A process for the preparation of N-benzylamines, in which
   (i) in a first step, a benzaldehyde is reacted with a primary amine to give the imine and
   (ii) in a second step, the imine is hydrogenated with hydrogen in the presence of a catalyst containing one or more metals of groups 8 to 10 of the Periodic Table of the Elements to give the N-benzylamine,
   wherein the iminization (i) is carried out in a water-miscible solvent and the resulting water of reaction is not removed, and the hydrogenation (ii) is carried out in the imine solution obtained in the iminization (i) and containing water of reaction.

2. A process for the preparation of N-benzylamines of the formula (I)

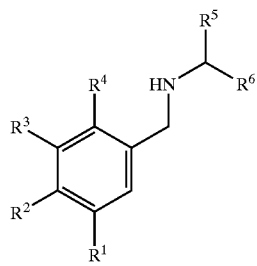

where
$R^1$, $R^2$, $R^3$ and $R^4$, independently of one another, are each H, halogen or $C_1$–$C_4$-alkyl or $C_1$–$C_4$-alkoxy each of which is unsubstituted or mono- or polysubstituted by halogen,
$R^5$ is H or $C_1$–$C_8$-alkyl and
$R^6$ is H, $C_1$–$C_8$-alkyl or $C_5$–$C_{12}$-aryl or $C_5$–$C_{12}$-cycloalkyl, each of which may be mono- or polysubstituted by halogen, OH or $C_1$–$C_4$-alkyl and/or $C_1$–$C_4$-alkoxy each of which is unsubstituted or mono- or polysubstituted by halogen, or is $C_1$–$C_4$-alkoxy- or benzyloxy-substituted $C_1$–$C_4$-alkyl,
in which
(i) in a first step, a benzaldehyde of the formula (II) is reacted with an amine of the formula (III)

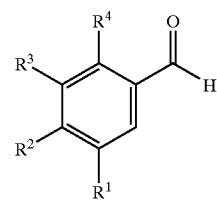

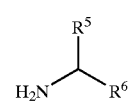

to give the imine of the formula (IV)

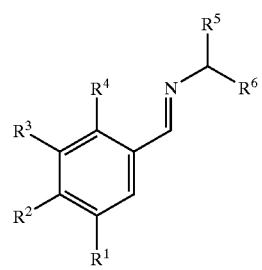

where
$R^1$–$R^6$ have the abovementioned meanings, and
(ii) in a second step, the imine of the formula (IV) is hydrogenated with hydrogen in the presence of a catalyst containing one or more metals of groups 8 to 10 of the Periodic Table of the Elements to give the N-benzylamine of the formula (I),
wherein the iminization (i) is carried out in a water-miscible solvent and the resulting water of reaction is not removed, and the hydrogenation (ii) is carried out in the imine (IV) solution obtained in the iminization (i) and containing water of reaction.

3. A process as claimed in claim 1, wherein the water-miscible solvent is selected from the group consisting of methanol, ethanol, n-propanol, isopropanol, glycol, tert-butanol, THF, glycol monoalkyl ethers and glycol dialkyl ethers.

4. A process as claimed in claim 1, wherein the catalyst used is palladium on active carbon.

5. A process as claimed in claim 2, wherein the aldehyde of the formula (II) is selected from the group consisting of benzaldehyde, 4-methoxybenzaldehyde, 4-tert-butylbenzaldehyde, 4-methylbenzaldehyde, 4-chlorobenzaldehyde, 4-fluorobenzaldehyde, 3-fluorobenzaldehyde, 3,5-difluorobenzaldehyde, 4-trifluoromethylbenzaldehyde and 3,5-bistrifluoromethylbenzaldehyde.

6. A process as claimed in claim 2, wherein the amine of the formula (III) is selected from the group consisting of α-phenylethylamine, 1-(4-methylphenyl)ethylamine, 2-heptylamine, 1-(4-chlorophenyl)ethylamine, 1-phenylpropylamine, 2-amino-3,3-dimethylbutane, 1-(1-naphthyl)ethylamine, 1,2,3,4-tetrahydronaphthylamine, 1-(4-methoxyphenyl)ethylamine, aminocyclopentanol, aminocyclohexanol, 1-aminoindane, 1-(2,4-dichlorophenyl)ethylamine, 1-benzyloxy-2-propylamine, 1-(2-naphthyl)ethylamine, 1-(3,5-bistrifluoromethylphenyl)ethylamine and 1-(4-fluorophenyl)ethylamine.

7. A process as claimed in claim 1, wherein the iminization (i) is carried out at from 10 to 40° C. and at atmospheric pressure.

* * * * *